(12) United States Patent
Li et al.

(10) Patent No.: US 6,899,731 B2
(45) Date of Patent: May 31, 2005

(54) CONTROLLED DELIVERY OF THERAPEUTIC AGENTS BY INSERTABLE MEDICAL DEVICES

(75) Inventors: Weiping Li, Salt Lake City, UT (US); Hai-Quan Mao, Singapore (SG); Kam W. Leong, Ellicott City, MD (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 228 days.

(21) Appl. No.: 09/750,779

(22) Filed: Jan. 2, 2001

(65) Prior Publication Data
US 2002/0061326 A1 May 23, 2002

Related U.S. Application Data
(60) Provisional application No. 60/173,743, filed on Dec. 30, 1999.

(51) Int. Cl.$^7$ ............................. A61F 2/06; A61K 48/00
(52) U.S. Cl. ...................... 623/1.42; 514/44; 435/320.1
(58) Field of Search ...................... 423/320.1; 435/455, 435/320.1; 514/44, 2; 424/486, 93.2; 623/1.42, 1; 604/51

(56) References Cited

U.S. PATENT DOCUMENTS

| | | | | |
|---|---|---|---|---|
| 5,516,781 | A | | 5/1996 | Morris et al. |
| 5,578,073 | A | * | 11/1996 | Haimovich .................... 623/1 |
| 5,652,225 | A | * | 7/1997 | Isner .......................... 514/44 |
| 6,004,943 | A | * | 12/1999 | Shi ............................. 514/44 |
| 6,013,780 | A | * | 1/2000 | Neufeld ...................... 536/23.1 |
| 6,099,562 | A | * | 8/2000 | Ding et al. ................. 623/1.46 |
| 6,127,448 | A | * | 10/2000 | Domb ......................... 523/105 |
| 6,468,304 | B1 | * | 10/2002 | Dubois-Rande et al. ... 623/1.42 |
| 6,589,546 | B2 | * | 7/2003 | Kamath et al. ............. 424/423 |
| 2002/0028243 | A1 | * | 3/2002 | Masters ...................... 424/484 |

FOREIGN PATENT DOCUMENTS

| | | |
|---|---|---|
| EP | 0 939 319 A2 | 9/1999 |
| JP | 11-316225 | 11/1999 |
| WO | WO 99/08729 | 2/1999 |
| WO | WO 99/59649 | 11/1999 |
| WO | WO 00/62830 | 10/2000 |

OTHER PUBLICATIONS

Anderson et al., Nature, vol. 392, Apr. 25–30, 1998.*
Rosenberg, Science, vol. 287, p. 1751, 2000.*
Verma et al. (Nature, vol. 389, Sep. 18, 1997, pp. 239–242).*
F. Dosio, et al., "Preparation, characterization and properties in vitro and in vivo of a paclitaxel-albumin conjugate", Journal of Controlled Release, 1997, pp 293–304, vol. 47. (Elsevier Science Publishers B. V. Amsterdam).

* cited by examiner

Primary Examiner—Dave T. Nguyen
(74) Attorney, Agent, or Firm—Kenyon & Kenyon

(57) ABSTRACT

A medical device and method for transportation and release of a therapeutic agent into a mammalian body are disclosed. The medical device is coated with alternating layers of a negatively charged therapeutic agent and a cationic polyelectrolyte, following a controlled adsorption technique. The method is simple, with minimal perturbation to the therapeutic agent and uses clinically acceptable biopolymers such as human serum albumin. The amount of the therapeutic agent that can be delivered by this technique is optimized by the number of the layers of the therapeutic agent adsorbed on the surface of medical device. There is a washing step between alternate layers of the therapeutic agent and cationic polyelectrolyte carrier, so that the amount of the therapeutic agent on the insertable medical device represents the portion that is stably entrapped and adsorbed on to the medical device. The insertable medical device and method according to this invention are capable of reproducibly delivering therapeutic agent to a site in a mammalian body, and allow for a highly reproducible and controllable release kinetics of the therapeutic agent.

57 Claims, 5 Drawing Sheets

CONTROLLED DELIVERY OF THERAPEUTIC AGENTS BY INSERTABLE MEDICAL DEVICES

This application claims the benefit of Provisional Application No. 60/173,743, filed Dec. 30, 1999.

BACKGROUND

1. Field of the Invention

The present invention relates to the localized delivery of negatively charged therapeutic agents, and more particularly to the localized and controlled delivery of DNA absorbed to the surface of insertable medical devices, in particular, balloon catheters or stents.

2. Background of the Invention

It is often desirable to administer drug agents at localized sites within the body because the systemic administration of drug agents treats the body as a whole even though the disease to be treated may be localized. Various methods have been proposed for such localized drug administration. For example, U.S. Pat. No. 5,304,121, which is incorporated herein by reference, discloses a method of delivering water-soluble drugs to tissue at desired locations of a body lumen wall. The method generally includes the steps of impregnating a hydrogel polymer on a balloon catheter with an aqueous drug solution, inserting the catheter into a blood vessel to a desired location, and expanding the catheter balloon against the surrounding tissue to allow the release of the drug.

One potential drawback to conventional localized drug administration is the uncontrolled manner at which the drug or drug solution is released from the delivery device. It is often desired, if not necessary, to control and/or lengthen the time period over which the drug is released. For example, it might be advantageous to lengthen the release time from seconds to minutes, or from minutes to hours, days, or even weeks. Exceptionally long release times as long as several months are often desired, for example, where the drug is released from an implanted device such as a stent. Moreover, it is often desired to control the release rate of the drug over prolonged periods of time.

Gene therapy provides an alternative approach to combating many intractable cardiovascular diseases. A site-specific delivery of the genetic vectors to minimize systemic complications is crucial for the therapeutic potential of this approach to be realized. Advances in interventional radiology and innovative designs in balloon angioplasty and stents have raised that possibility.

The invention disclosed herein solves the potential drawbacks to the drug delivery methods and instruments of the prior art by providing novel apparatus and methods for the transfer of therapeutic agents, such as therapeutic genes, to internal body sites. The apparatus of the invention may be guided to diseased or deficient organs, or other lesions, and deliver the therapeutic agent in a targeted and controlled manner.

SUMMARY OF THE INVENTION

In one aspect, the present invention provides a method of delivering a negatively charged therapeutic agent to a target location within a mammalian body. The method comprises the steps of applying a multiplicity of alternating layers of at least one cationic polyelectrolyte carrier and a multiplicity of layers of a negatively charged therapeutic agent to at least one surface of an insertable medical device. A washing step is employed between application of the cationic polyelectrolyte and the negatively charged therapeutic agent. The medical device is delivered to a target site within the body, and upon reaching the target site the negatively charged therapeutic agent is released into the target site. The negatively charged therapeutic agent remains qualitatively and quantitatively intact during the stages of coating, washing, delivery and release.

In a preferred embodiment of this invention, the at least one cationic polyelectrolyte carrier is human serum albumin, gelatin, chitosan or a combination thereof.

In a more preferred embodiment of this invention, the outer coating layer of the cationic polyelectrolyte carrier is chitosan, gelatin or both, which cationic polyelectrolyte carriers affect the time of release of the negatively charged therapeutic agent from the insertable medical device upon delivery. The length of the time lag could be controlled by the type and amount of the cationic polyelectrolyte carrier used.

The device of this invention may compose a negatively charged, neutral, or positively charged structure such as polystyrene, polyethylene film, or glass. In a preferred embodiment of this invention, a balloon catheter, having a balloon in a diameter of about 0.4 cm, and a length of about 1.5, is used.

In yet another preferred embodiment of this invention, the negatively charged therapeutic agent is a polynucleotide and in a more preferred embodiment of this invention, the polynucleotide is a naked DNA, DNA inserted into a viral or non-viral vectors.

Another preferred embodiment of this invention provides an insertable medical device for insertion into a mammalian body, wherein the insertable medical device has a multiplicity of alternating layers of at least one cationic polyelectrolyte and a biologically effective amount of a negatively charged therapeutic agent, which are adsorbed on to a surface of the insertable medical device. The amount of adsorbed negatively charged therapeutic agent increases linearly with the number of the layers of same applied and entrapped onto the surface of the medical device.

In a preferred embodiment of this invention, the insertable medical device is, for example, a stent or a balloon catheter. In a more preferred embodiment of this invention an outer coating of the insertable medical device is employed to delay the release of the negatively charged therapeutic agent. The outer coating is preferably gelatin, and more preferably chitosan.

In another aspect of this invention, there is provided a method for delivering a therapeutic agent that prevents or treats angiogenesis, restenosis, cardiomyopathy, cystic fibrosis, or malignant cell proliferation.

Figure 1:
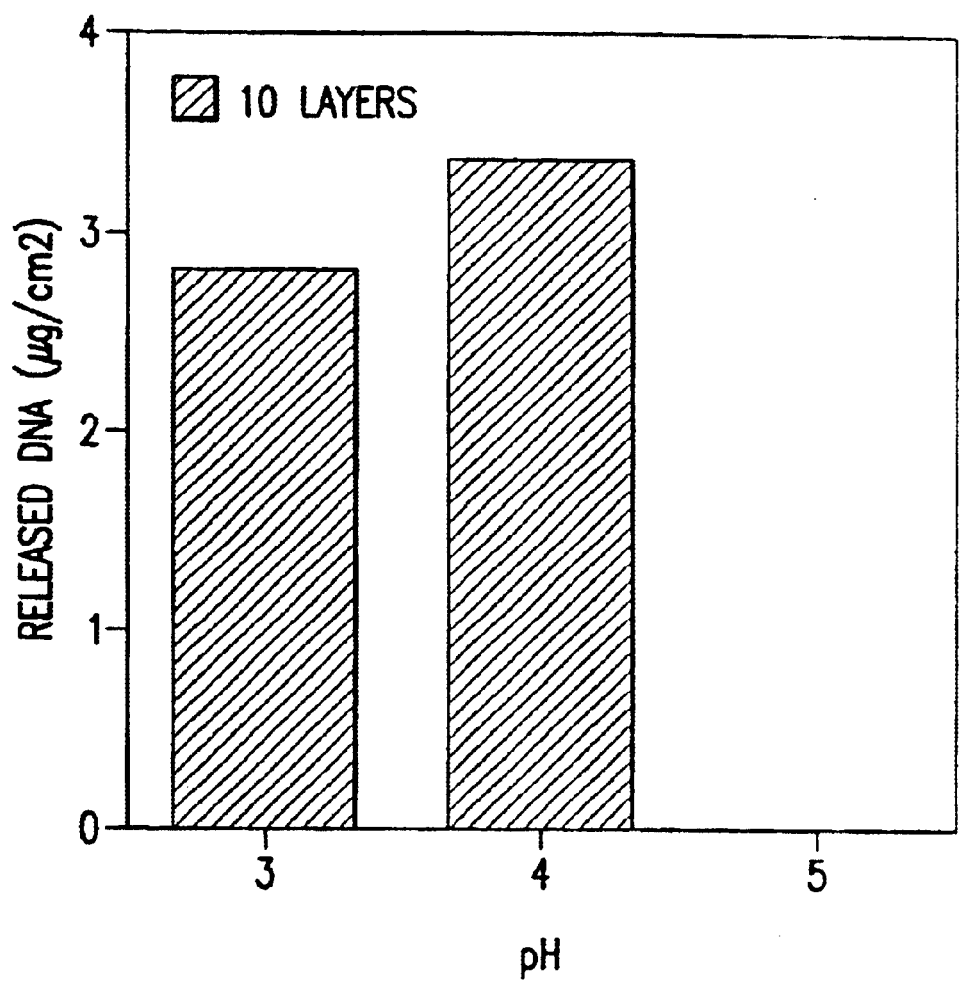
FIG. 1 is a histogram showing the effect of pH on the amount of DNA released from the surface of an insertable device. The amount of released DNA from 10 layers of coating was measured at pH 3 and 4.

1: pRE-Luc+Lipofectamine; 2: pRE-Luc released from the balloon+Lipofectamine;

3: pRE-Luc; 4: DNA+Chitosan coated surface; 5: DNA+gelatin coated surface; 6: DNA coated surface.

DETAILED DESCRIPTION OF THE INVENTION

Definitions

As used herein, the following terms are defined as follows:

"Therapeutic agent" as used herein includes any compounds or compositions that induce a biological/medical reaction in vitro, in situ, or in vivo settings.

"Negatively charged therapeutic agent" as used herein, encompasses therapeutic agents that are negatively charged, either naturally or synthetically. A negative charge may be added by any known chemical means or biological means (i.e., addition or deletion of functionalities, substitutions, or mutations).

"Therapeutic polynucleotide" as used herein includes nucleic acids with and without carrier vectors, compacting agents, virus, polymers, proteins, or targeting sequences.

"Stenosis" refers to a stricture of any bodily canal.

"Stent" refers to any tubular structure used to maintain or support a bodily orifice or cavity.

"Balloon catheter" refers to a tubular instrument with a balloon or multiple balloons that can be inflated or deflated without removal after insertion into the body.

"Washing solution" according to this invention is water, any suitable buffers or detergents, solvents or a combination thereof.

"Surface" according to this invention means any portions of any parts of an insertable medical device, or a combination of different portions of different surfaces, of an insertable medical device.

"Effective expression-inducing amount", as described herein, means amount of a polynucleotide that effectuates expression of a polypeptide encoded by a gene contained in such polynucleotide.

"Qualitatively and quantitatively intact", as described herein, means substantially the same biological activity and substantially the same amount. Substantially means at least about 90%.

Detailed Description of the Invention

This invention describes a medical device and a method to deliver a negatively charged therapeutic agent within the vasculature of a patient. The negatively charged therapeutic agent is adsorbed onto one or more sites or surfaces of a medical device, thereby forming a coated surface, by a controlled adsorption technique. When the coated surface(s) comes into contact with the patient's blood, the negatively charged therapeutic agent is released with a short controlled lag time of about 1 to several minutes (for example, 1,5 or 10 minutes) to allow the medical device to reach the target site.

The method and medical device of this invention, as described herein, maximize the amount of a negative therapeutic agent that can be adsorbed to the medical device and control the release of the negatively charged therapeutic agent, with only minimal perturbation, at the target site. The method and medical device, as described herein, use clinically acceptable polyelectrolytes biopolymers such as human serum albumin (HSA) to build the negatively charged therapeutic agent onto the surface of medical device.

Washing is employed between application of each alternate layers of one or more polyelectrolytes and the negatively charged therapeutic agent. Washing ensures that the negatively charged therapeutic agent is stably entrapped and not just precipitated on the surface of the device. This method of coating the medical device provides a more reproducible and controllable adsorption and release kinetics of a negatively charged therapeutic agent adsorption and release.

The medical device used in this invention is any insertable medical device, including, for example, stents, catheters, or balloon catheters. A preferred medical device for use with the present invention is a balloon catheter. The medical device of this invention can be used, for example, in any application for treating, preventing, or otherwise affecting the course of a disease or tissue or organ dysfunction. For example, the medical instrument of the invention can be used to induce or inhibit angiogenesis, or to prevent or treat restenosis, cardiomyopathy, or other dysfunction of the heart, and is particularly applicable to angioplasty treatment.

Additionally, the method and medical device described herein can be used, for example, in treating cystic fibrosis or other dysfunction of the lung, for treating or inhibiting malignant cell proliferation, for treating any malignancy, and for inducing nerve, blood vessel or tissue regeneration in a particular tissue or organ.

Specific examples of the negatively charged therapeutic agent used in conjunction with the present invention includes, for example, any negatively charged compounds or compositions that are negatively charged, either naturally or synthetically by means of known chemical methods. In particular, the terms "therapeutic agents" and "drugs" are used interchangeably herein and include pharmaceutically active compounds and compositions, polynucleotides with and without carrier vectors such as lipids, compacting agents (such as histones), virus, polymers, proteins, and the like, with or without targeting sequences.

Specific examples of the polynucleotide used in conjunction with the present invention include, for example, oligonucleotides, ribozymes, anti-sense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a non-infectious vector or in a viral vector and which further may have attached peptide targeting sequences; antisense nucleic acid (RNA or DNA); and DNA chimeras which include gene sequences and encoding for ferry proteins such as membrane trans locating sequences ("MTS") and herpes simplex virus-1 ("VP22"),and constitutive housekeeping genes which are theoretically expressed in all cell types.

Non-limiting examples of virus vectors or vectors derived from viral sources include adenoviral vectors, herpes simplex vectors, papilloma vectors, adeno-associated vectors, retroviral vectors, and the like. The use of adenovirus is particularly preferred.

Other examples of the therapeutic agent include any of the following compounds and compositions, provided that they are made to be negatively charged, using any known chemical and/or biological method. Any of these modifications is routinely made by one skilled in the art. These compounds include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, andnitorfurantoin; anesthetic agents such as lidocaine, bupivacaine, and ropivacaine; nitric oxide (NO) donors. such as lisidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptide-containing compound, heparin, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; survival genes which protect against cell death, such as anti-apoptotic Bcl-2 family factors and Akt kinase; and combinations thereof Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body.

In addition, the polypeptides or proteins, DNA of which can be incorporated, include without limitation, angiogenic factors and other molecules competent to induce angiogenesis, including acidic and basic fibroblast growth factors, vascular endothelial growth factor, hif-1, epidermal growth factor, transforming growth factor α and β, platelet-derived endothelial growth factor, platelet-derived growth factor, tumor necrosis factor α, hepatocyte growth factor and insulin-like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-I"), and the family of bone morphogenic proteins ("BMP's"). The known proteins include BMP-2, BMP-3, BMP-4, BMP-5, BMP-6 (Vgr-1), BMP-7 (OP-I),BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA's encoding them.

The amount of polynucleotide adsorbed is an effective expression-inducing amount. As used herein, the term "effective expression-inducing amount" means that amount of the polynucleotide that effectuates expression of a gene product encoded by such polynucleotide. Means for determining an effective expression-inducing amount of a polynucleotide are well known in the art. For example, an effective expression-inducing amount of the polypeptide of this invention is from about 0.3 to about 10 $\mu g/cm^2$/layer, preferably from about 0.5 to about 0.9 $\mu g/cm^2$/layer. The amount of polynucleotide adsorbed onto the. surface of the medical device is linearly proportional to the number of layers applied thereto. At least up to 40 layers of a therapeutic agent could be applied without affecting the properties of the medical device. Preferably from about 4 to about 60 layers, more preferably from about 10 to about 50 layers and most preferably from about 20 about 40 layers of a therapeutic agent are applied.

Polynucleotides, for example, naked DNA, DNA plus vector or DNA deliyery complex is captured on the surface of the medical device by a cationic polyelectrolyte carrier. Viral or non-viral vectors could be used to potentiate the transfection efficiency of the released DNA. For example, a virus culture, such as adenovirus could be layered on the surface of the insertable medical device. The concentration of the virus solution significantly affects the amount of the viral particles, which is incorporated into the layers on the surface of the insertable medical device. The release kinetics are reproducible and controlled. The released DNA is bioactive with little decrease of potency.

Biological activity of the DNA released from the medical device was studied by transfection of HEK 293 cells in vitro. The results indicated that the biological activity of the released DNA was the same as the control. Similar controlled-adsorption techniques were used to adsorb adenoviruses on to the balloon surface.

Any suitable surface of the medical instrument may be coated. The surfaces to be coated may comprise any medically acceptable material, such as, for example, carboxylated and aminated polystyrene, and silanized glass.

As cationic polyelectrolyte carriers, any medically acceptable polymers or copolymers, or natural polymers such as human serum albumin, gelatin, chitosan and the like may be used. The natural polymers are adsorbed onto a desired surface of the medical device for coating. It is not necessary that an entire surface is coated, rather, merely a portion of a surface may be coated.

The coated medical device is inserted into the patient and directed to the target site. When the coated surface comes into contact with blood, the charge interaction of the cationic polymer and the negatively charged therapeutic agent is disrupted due to a charge screening effect and because the charge density of the polymer is greatly decreased at physiological pH. In addition, proteolytic degradation of the gelatin or HAS may also contribute to the dissociation of the polymer-drug complex.

To delay dissociation of the adsorbed therapeutic agent when a medical device coating with same is inserted into the blood stream, a more cationic and more hydrophobic polymer layer can be applied at the outer coating. The quantity and quality of the biopolymer, particularly, the outer biopolymer, is directly proportional to the duration of lag time achieved before the release occurred. Chitosan, a natural polysaccharide derived from crab shells, was used and shown to serve this purpose. Other polymers can also be used to fine-tune the release kinetics of the therapeutic agent from the coated surface. For example, with a thin coaating of condensed gelatin or chitosan, a short lag time of about 1–2 minutes is achieved before release occurs . Without the use of gelatin or chitosan, 100% of the DNA is released at physiological pH within minutes.

Organs and tissues that are treated by the methods of the present invention include any mammalian tissue or organ, whether injected in vivo or ex vivo. Non-limiting examples include the heart, lung, brain, liver, skeletal muscle, smooth muscle, kidney, bladder, intestines, stomach, pancreas, ovary, prostate, cartilage and bone.

The negatively charged therapeutic agents, according to the invention, can be used, for example, in any application for treating, preventing, or otherwise affecting the course of a disease or tissue or organ dysfunction. For example, the methods of the invention can be used to induce or inhibit angiogenesis, as desired, to prevent or treat restenosis, to treat a cardiomyopathy or other dysfunction of the heart, for treating cystic fibrosis or other dysfunction of the lung, for treating or inhibiting malignant cell proliferation, for treating any malignancy, and for inducing nerve, blood vessel or tissue regeneration in a particular tissue or organ. Particularly, the negatively charged therapeutic agents of this invention are used preferably in angioplasty. Having now fully described the invention, the same would be more readily understood by reference to specific examples which are provided by way of illustration, and not intended to be limiting of the invention, unless herein specified.

EXAMPLE 1

Effect of Surfaces and Polyelectrolytes on the DNA Release

Multilayered films of DNA were built up on various negatively charged, neutral, and positively charged surfaces, by spraying or dipping. The DNA adsorbed by HSA or gelatin was released quickly whereas, due to the hydrophobicity of chitosan at neutral pH, the DNA adsorbed by chitosan was released very slowly. The result of this experiment is tabulated in Table I below. Table 1 shows natural polymers, as polyelectrolytes, are coated onto several surfaces, which surfaces were modified by different substrates. When different surfaces were dipped into a slightly acidic solution containing a polynucleotide, the positively charged coated surface induced adsorption of the polynucleotide (i.e., adsorption was driven by the charged interaction). Successive layering of the surface with polyelectrolyte and DNA can be repeated as many times as needed to maximize the amount of DNA adsorbed to the surface. The alternate layers of polyelectrolyte and polynucleotide are stable in a solution that is slightly acidic and of low ionic strength.

TABLE 1

The amount of DNA release with different polyelectrolyte combinations and substrates

| Substrate | Formulation | Number of layers | Amount of DNA released ($\mu g/cm^2$) |
|---|---|---|---|
| PEG/gelatin-modified Glass | Gelatin/DNA | 4 | 1.23 (overnight) |
| Carboxylated PS | HSA/DNA | 4 | 1.24 (0.5 hr) |
| Polyethylene film | HSA/DNA | 4 | 1.14 (0.5 hr) |
| PET balloon | HSA/DNA | 4 | 1.29 (0.5 hr) |
| PET balloon | HSA/DNA | 10 | 3.28 (overnight) |
| PET balloon | Gelatin/DNA | 10 | 2.62/5.13 (0.5 hr/4 d) |
| PET balloon | Chitosan/DNA | 20 | 0/0.86 (1 hr/17 hrs) |

EXAMPLE 2

Effects of pH on the Amount of DNA Released

Figure 2:
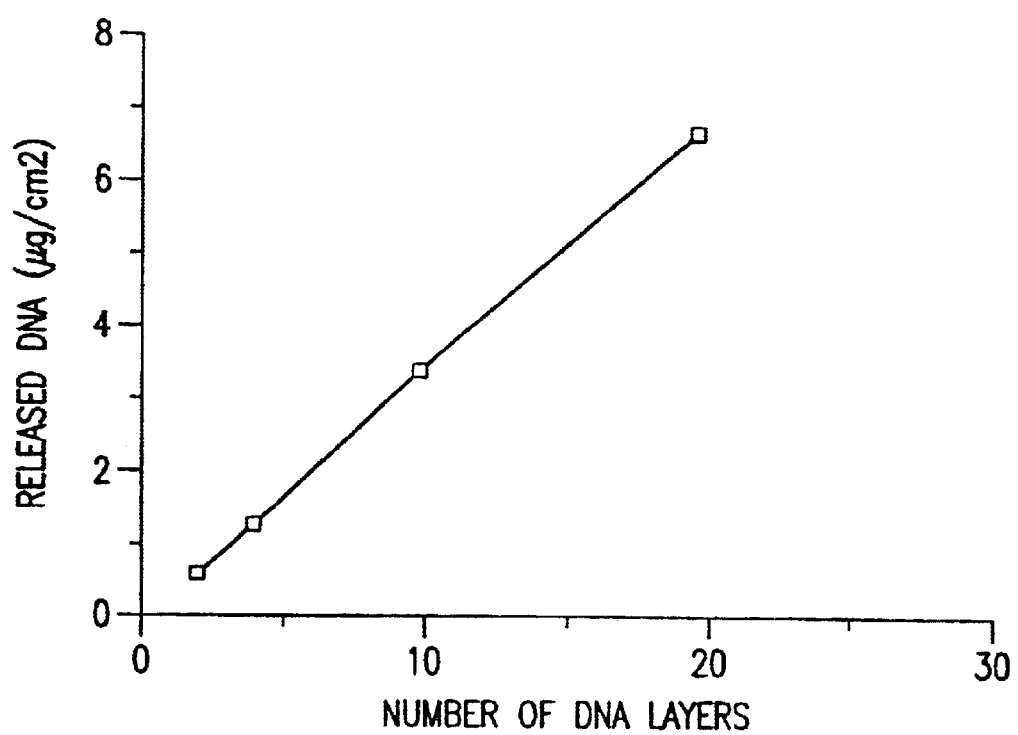
FIG. 2 is a graph showing the relationship between the number of DNA layers and the amount of DNA adsorbed on the surface of a medical device. Released DNA was measured against the number of layers of DNA coatings on the surface of the medical device.

The effect of pH on the amount of DNA adsorbed was investigated by alternating adsorption of DNA and HSA at different pHs. The results, as shown in FIG. 1, indicated that HSA adsorption is optimal at pH 4.0; no DNA could be adsorbed at pH 5.0 or higher. The relationship between the number of DNA layers and adsorbed amount of DNA was investigated by alternating adsorption of DNA and HSA at pH4.0. The results, as demonstrated in FIG. 2, showed that the amount of DNA absorbed increased linearly with the number of DNA layers on the surface of the medical device.

EXAMPLE 3

The Release Kinetics of the Adsorbed DNA from the Surface of the Medical Device

Figure 3:
FIG. 3 is a photographic image of a DNA coated balloon catheter (ethydium bromide stained) before and after the DNA release. 1: DNA coated balloon catheter (stained with ethydium bromide); 2: DNA coated balloon catheter after in vitro release stained with ethydium 20 bromide; and 3: control uncoated balloon catheter.
Figure 4:
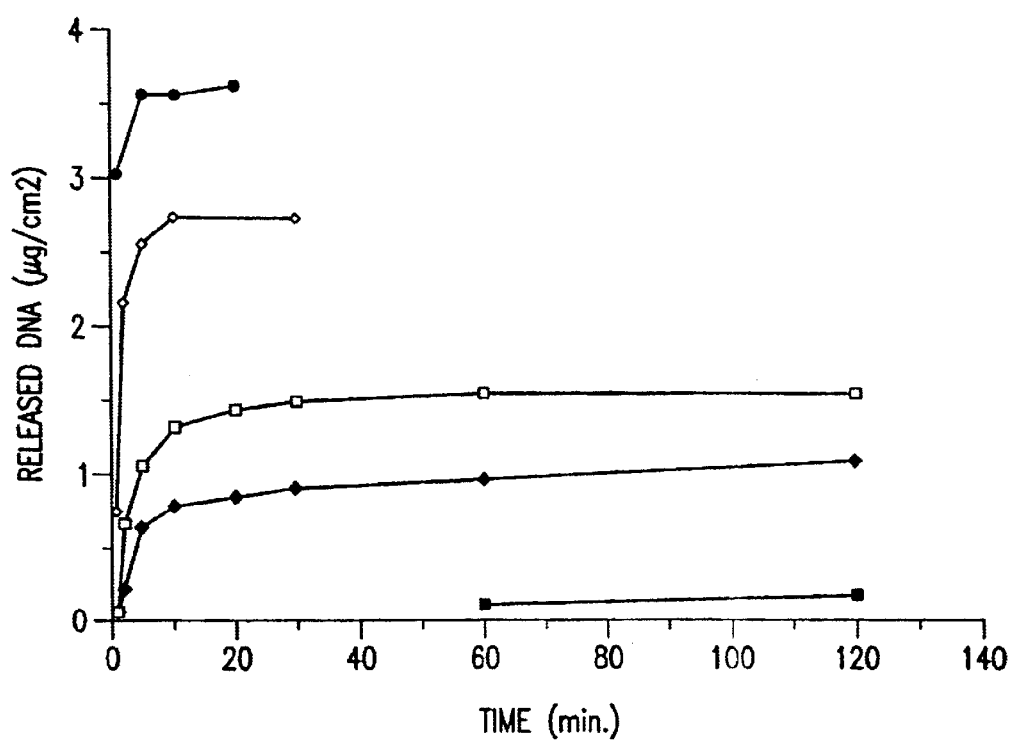
FIG. 4 is a graph showing release kinetics studies using gelatin or chitosan coatings
- ■ without outer coating
- ◇ with gelatin coating (2%)
- □ with chitosan coating (10 ppm)
- ◇ with chitosan coating (20 ppm)
- ◘ with chitosan coating (40 ppm)

Release kinetics studies indicated that the adsorbed polynucleotide could be released completely within 5 minutes. (See FIG. 3 which shows that the adsorbed DNA was released almost completely from the surface of a coated balloon catheter.) When the medical device is coated with a condensed gelatin coating, the release rate of the adsorbed DNA was reduced slightly, whereas when the device was coated with a thin layer of chitosan, the release rate of the adsorbed DNA was decreased remarkably. The release kinetics of the adsorbed DNA, as shown in FIG. 4, was also shown to be dependant on the thickness of chitosan coating (i.e., the concentration of chitosan solution when the dipping time was fixed).

EXAMPLE 4

Biological Activity of the Released DNA

Figure 5:
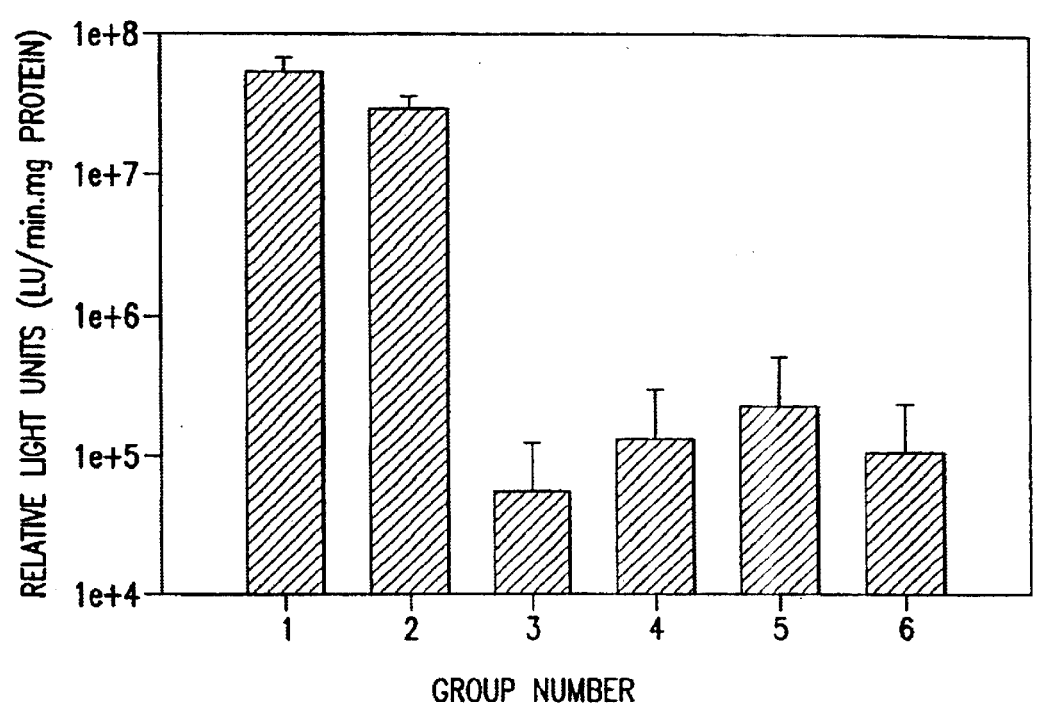
FIG. 5 is a histogram showing transfection rate of HEK 293 cells with DNA released from a balloon medical device. Columns 1–6 each represents the following.

The biological activity of DNA, released from the surface of a coated medical device, was investigated by transfecting HEK 293 cells in vitro. The result of this study, as shown in FIG. 5, indicates that the released DNA was still biologically active. A comparison between columns 1 and 2 of FIG. 5 shows that the DNA released from the medical device coated with gelatin or chitosan, similar to the naked DNA, had a high transfection efficiency. Occasionally, cationic gelatin complexes with DNA in the soluble form and transfects cells in culture better than naked DNA.

EXAMPLE 5

Feasibility of Delivering Adenovirus

Using similar adsorption technique with gelatin as the polycation, $^{125}$I labeled recombinant adenovirus, encoding the Lac Z gene, was adsorbed onto a balloon surface. The result of this experiment is shown in Table 2 below. Table 2 indicates that the amount of plaque forming units and virus particles of adenovirus, released or remained on the balloon after release delivery, constitutes a major portion of the total amount of virus found on the surface of the balloon.

TABLE 2

Feasibility of delivering adenovirus

|  | Readings | Total amount of virus | | Amount of adenovirus | |
| --- | --- | --- | --- | --- | --- |
|  |  | (pfu) | (particles) | (pfu/cm$^2$) | (vp/cm$^2$) |
| Calibration Standard | 538.5 ± 52 | 6.4 ± 0.6 × 10$^7$ | 1.6 ± 0.2 × 10$^9$ | — | — |
| Released adenovirus | 47 ± 9.5 | 5.6 ± 1.1 × 10$^6$ | 1.4 ± 0.3 × 10$^8$ | 4.0 ± 0.8 × 10$^6$ | 1.0 ± 0.2 × 10$^8$ |
| Virus remained balloon after release | 168.5 ± 58 | 2.0 ± 0.7 × 10$^7$ | 5.0 ± 1.7 × 10$^8$ | 1.4 ± 0.5 × 10$^7$ | 3.5 ± 1.2 × 10$^8$ |

Table 2 shows the amount of adenovirus released in 60 minutes in 10% serum culture media from a 10-layered balloon.

EXAMPLE 6

DNA Delivery Via Negatively Charged Polystyrene (PS) Surface

Carboxylated polystyrene (PS) wells were treated with 360 μl (per well) of 0.1% human serum albumin (HSA) in 25 mM HAc—NaAc/25 mM Na$_2$SO$_4$ buffer (pH 4.0) at room temperature (RT) overnight. The wells were washed thoroughly with water and then treated with 360 μl (per well) of DNA (247 μg/ml) in 25 mM HAc—NaAc/25 mM Na$_2$SO$_4$ buffer (pH 4.0) at RT for 0.5 hr. The wells were washed once with 360 μl (per well) of 25 mM HAc—NaAc/25 mM Na$_2$SO$_4$ buffer (pH 4.0) and then treated again with 360 μl of 0.1% HSA in 25 mM HAc—NaAc/25 mM Na$_2$SO$_4$ buffer (pH 4.0) at RT for 0.5 hr. The wells were washed once with 360 μl (per well) of 25 mM HAc—NaAc/25 mM Na$_2$SO$_4$ buffer (pH 4.0) and then treated again with 360 μl (per well) of DNA (247 ug/ml) in 25 mM HAc—NaAc/25 mM Na$_2$SO$_4$ buffer (pH 4.0) at RT for 0.5 hr. The preceding washing steps were repeated until multilayer of DNA layers were adsorbed. The wells were washed once with 360 μl (per well) of 25 mM HAc—NaAc/25 mM Na$_2$SO$_4$ buffer (pH 4.0) and then treated with 360 μl of 1 X phosphate buffered saline (PBS) at RT for 0.5 hr. The amount of DNA released in PBS was determined, and shown in Table 3 below.

TABLE 3

Relationship between the number of DNA layers and the amount of DNA Released

|  | A | B | C | D |
| --- | --- | --- | --- | --- |
| Number of DNA layers | 1 | 2 | 3 | 4 |
| Released DNA (μg/cm$^2$) | 0.105 | 0.493 | 0.806 | 1.240 |

EXAMPLE 7

DNA Delivery via Positively Charged Glass Surface

Two pieces of polyethylene glycol (PEG)/gelatin-modified glass plates were treated with 2 ml of DNA (140 μg/ml) in 25 mM HAc—NaAc/25 mM Na$_2$SO$_4$ buffer (pH 5.5) at 37° C. for 1 hr. The plates were washed once with 3 ml of 25 mM HAc—NaAc/25 mM Na$_2$SO$_4$ buffer (pH 4.0) and then treated with 2 ml of 0.05% gelatin (A, 175) in 25 mM HAc—NaAc/25 mM Na$_2$SO$_4$ buffer (pH 4.8) at 37° C. for 1 hr. The plates were washed once with 3 ml of 25 mM HAc—NaAc/25 mM Na$_2$SO$_4$ buffer(pH 4.0) and then treated again with 2 ml of DNA (88 μg/ml) in 25 mM HAc—NaAc/25 mM Na$_2$SO$_4$ buffer (pH 5.5) at 37° C. for 1 hr. The preceding washing steps were repeated until several layers of DNA layers were adsorbed. The plates were washed once with 3 ml of 25 mM HAc—NaAc/25 mM Na$_2$SO$_4$ buffer (pH 4.0) and then dipped in 2 ml of 1× PBS at RT for 1 hr. The amount of DNA released in PBS is shown in Table 4 below.

TABLE 4

DNA release from glass surface.

|  | A | B |
| --- | --- | --- |
| Number of DNA layers | 4 | 9 |
| Released DNA (μg/cm$^2$) | 1.231 | 3.923 |

EXAMPLE 8 cDNA Delivery via Neutral PET Balloon Surface

Two balloons (each having the diameter of 0.4 cm, length of 1.5 cm, and a surface area of ca. 1.88 cm$^2$) were treated with 5 ml of 0.1% HSA in 25 mM HAc—NaAc/25 mM Na$_2$SO$_4$ buffer (pH 4.0) at RT for 2 hours. The balloons were washed thoroughly with water and then treated with 5 ml of DNA (141 μg/ml, p 43 hGFP) in 25 mM HAc—NaAc/25 mM Na$_2$SO$_4$ buffer (pH 4.0) at RT for 0.5 hr. The balloons were washed once with 5 ml of 25 mM HAc—NaAc/25 mM $Na_2SO_4$ buffer (pH 4.0) and then treated again with 5 ml of 0.1% HSA in 25mM HAc—NaAc/25 mM $Na_2SO_4$ buffer (pH 4.0) at RT for 0.5 hr. Balloons were washed once with 5 ml of 25 mM HAc—NaAc/25 mM $Na_2SO_4$ buffer (pH 4.0) and then treated again with 5 ml of DNA (141 μg/ml) in 25 mM HAc—NaAc/25 mM $Na_2SO_4$ buffer (pH 4.0) at RT for 0.5 hr. The preceding washing steps were repeated until 4 DNA layers were adsorbed. Results are tabulated in Table 5 below.

TABLE 5

DNA delivery on two balloons.

|  | A | B |
|---|---|---|
| Readings (ng/ml) | 55 | 54 |
| Released DNA (μg) | 2.42 | 2.376 |
| Released DNA (μg/cm$^2$) | 1.287 | 1.264 |

A: Balloon was washed once with 5 ml of 25 mM HAc-NaAc/25 mM $Na_2SO_4$ buffer (pH 4.0) and then dipped in 4 ml of 1 X PBS at RT for 0.5 hr.
B: Balloon was not washed and directly dipped in 4 ml of 1 X PBS at RT for 0.5 hr. The amount of DNA released in PBS was determined (200 μl was taken into 2 ml of test solution).

EXAMPLE 9

Transfection of HEK 293 Cells in Vitro

In a twelve-well tissue culture plate, 8×10$^4$ HEK 293 cells per well were seeded in 1 ml of the appropriate complete growth medium (10% serum) and incubated at 37° C. in a $CO_2$ incubator for 1 day. The culture medium was then removed and the transfection medium was added to the cells. The cells were then divided into 6 different groups:

Group 1: 2 μg of DNA (Luci) and 2 μl of lipofectamine in 1 ml of serum-free medium; Group 2: Released DNA (Luci, 20 layers) and 2 μl of lipofectamine in 1 ml of serum-free medium. Group 3: 2 μg of DNA (Luci) in 1 ml of serum-free medium. Group 4: Released DNA (Luci, 20 layers) with an outermost chitosan coating. Group 5: Released DNA (Luci, 20 layers) with an outermost gelatin coating. Group 6: Released DNA (Luci, 20 layers). The cells were incubated at 37° C. in a $CO_2$ incubator for three days. The media was removed from the cells and the cells were rinsed once with 1×PBS. Cell Culture Lysis (200 μl) was added at the concentration of 1×Reagent per well to cover the cells. The cells were incubated at room temperature for 10–15 minutes. The cell extract (about 20 μl) was added to a luminometer cuvette at room temperature, followed by 100 μl of Luciferase Assay Reagent, again at room temperature. The cuvette was placed in the luminometer. Light emission was measured for ten seconds. Protein concentration was determined using the Bio-Rad protein assay kit. The results, as shown in FIG. 5, were expressed as relative light units/min mg protein.

EXAMPLE 10

Adenovirus Adsorption

Two balloons [1.5 cm (L)×0.3 cm (D), 1.41 cm$^2$] were treated with 1 ml of 0.1% gelatin (A, 300) in 25 mM HAc—NaAc/25 mM $Na_2SO_4$ buffer (pH 5.0) at RT for 2 hours. The balloons were washed three times with 25 mM HAc—NaAc/25 mM $Na_2SO_4$ buffer (pH 5.0) and then treated with 1 ml of adenovirus (1.6×10$^9$ pfu/ml or 4×10$^{10}$ vp/ml containing a small amount of $^{125}$I-labeled adenovirus) in 25 mM HAc—NaAc/25 mM $Na_2SO_4$ buffer (pH 5.0) at RT for 2 minutes. The balloons were washed once with 1 ml of 25 mM HAc—NaAc/25 mM $Na_2SO_4$ buffer (pH 5.0) and then treated with 1 ml of 0.1% gelatin (A, 300) in 25 mM HAc—NaAc/25 mM $Na_2SO_4$ buffer (pH 5.0) at RT for 2 minutes. The balloons were washed once with 1 ml of 25 mM HAc—NaAc/25 mM $Na_2SO_4$ buffer (pH 5.0) and then treated again with 1 ml of adenovirus (1.6×10$^9$ pfu/ml or 4×10$^{10}$ vp/ml) containing a small amount of $^{125}$I-labeled adenovirus in 25 mM HAc—NaAc/25 mM $Na_2SO_4$ buffer (pH 5.0) at RT for 2 minutes. The preceding two steps were repeated until ten adenovirus layers were adsorbed. The balloons were washed once with 1 ml of 25 mM HAc—NaAc/25 mM $Na_2SO_4$ buffer (pH 5.0) and dipped in 1 ml of 10% serum culture medium for 60 min. The amount of adenovirus was determined by comparing the amount of radioactivity of $^{125}$I(10 ml of counting medium was used for each sample, Count 1 minute). The result of this experiment is shown in Table 5, above.

EXAMPLE 11

In Vivo Delivery of DNA to Heart

To stimulate angiogenesis or collateral blood flow in the adult rat heart, a balloon catheter, is coated with 40 layers of a DNA encoding human fibroblast growth factor-5 (hFGF-5) and is inserted into a blood vessel that perfuses the heart. Rats have been sacrificed at 3 weeks following injection and capillary density was measured by computerized light microscopy. The results have shown that a direct injection of a fibroblast growth factor-5 expression vector stimulates collateral vessel formation in areas of injected myocardium.

We claim:

1. An implantable medical device comprising a coating on at least a portion thereof, said coating comprising:
   an inner layer of a cationic polyelectrolyte carrier;
   a layer of at least one negatively charged therapeutic agent adsorbed onto said inner layer of a cationic polyelectrolyte carrier; and
   an additional layer or layers of a cationic polyelectrolyte carrier and an additional layer or layers of at least one negatively charged therapeutic agent adsorbed onto said additional layer or layers of a cationic polyelectrolyte carrier, wherein said additional layer or layers of a polyelectrolyte carrier and said additional layer or layers of at least one negatively charged therapeutic agent alternate.

2. The medical device of claim 1, further comprising an outermost layer of a cationic polyelectrolyte carrier which is the same or different from the inner or additional layer or layers of a cationic polyelectrolyte carrier.

3. The medical device of claim 2, wherein the outermost layer of a cationic polyelectrolyte carrier is more hydrophobic and/or more cationic than the inner or additional layer or layers of a cationic polyelectrolyte carrier.

4. The medical device of claim 1, wherein the inner or additional layer or layers of a cationic polyelectrolyte carrier comprises human serum albumin, gelatin, chitosan, or a combination thereof.

5. The medical device of claim 1, wherein the medical device comprises a stent, a catheter, a balloon catheter, or a combination thereof.

6. The medical device of claim 1, wherein the at least one negatively charged therapeutic agent comprises rapamycin.

7. The medical device of claim 1, wherein the at least one negatively charged therapeutic agent comprises paclitaxel.

8. A method of adsorbing at least one negatively charged therapeutic agent onto a medical device comprising:

(a) coating at least a portion of a medical device with a cationic polyelectrolyte carrier to form an inner layer of a cationic polyelectrolyte carrier;

(b) washing the inner layer of a cationic polyelectrolyte carrier with a washing solution;

(c) adsorbing at least one negatively charged therapeutic agent onto the inner layer of a cationic polyelectrolyte carrier to form a layer of at least one negatively charged therapeutic agent; and (d) washing the layer of at least one negatively charged therapeutic agent with a washing solution and repeating steps (a) through (c) one or more times to form multiple layers of a cationic polyelectrolyte carrier and at least one negatively charged therapeutic agent until a desired amount of at least one negatively charged therapeutic agent has been adsorbed onto the medical device.

9. The method of claim 8, further comprising the step of coating the outermost layer of the at least one negatively charged therapeutic agent with an outermost layer of a cationic polyelectrolyte carrier which is the same or different from the inner layer or multiple layers of a cationic polyelectrolyte carrier.

10. The method of claim 9, wherein the outermost layer of a cationic polyelectrolyte carrier is more hydrophobic and/or more cationic than the inner layer or multiple layers of a cationic polyelectrolyte carrier.

11. The method of claim 8, wherein the inner layer or multiple layers of a cationic polyelectrolyte carrier comprises a human serum albumin, gelatin, chitosan, or a combination thereof.

12. The method of claim 8, wherein the medical device comprises a stent, a catheter, a balloon catheter, or a combination thereof.

13. The method of claim 8, wherein the at least one negatively charged therapeutic agent comprises rapamycin.

14. The method of claim 8, wherein the at least one negatively charged therapeutic agent comprises paclitaxel.

15. A medical device comprising at least one negatively charged therapeutic agent adsorbed on at least a portion thereof and produced by a process comprising:

(a) coating at least a portion of a medical device with a cationic polyelectrolyte carrier to form an inner layer of a cationic polyelectrolyte carrier;

(b) washing the inner layer of a cationic polyelectrolyte carrier with a washing solution;

(c) adsorbing at least one negatively charged therapeutic agent onto the inner layer of a cationic polyelectrolyte carrier to form a layer of at least one negatively charged therapeutic agent; and (d) washing the layer of at least one negatively charged therapeutic agent with a washing solution and repeating steps (a) through (c) one or more times to form multiple layers of a cationic polyelectrolyte carrier and at least one negatively charged therapeutic agent until a desired amount of at least one negatively charged therapeutic agent has been adsorbed onto the medical device.

16. The medical device of claim 15, wherein the process further comprises the step of coating the outermost layer of the at least one negatively charged therapeutic agent with an outermost layer of a cationic polyelectrolyte carrier which is the same or different from the inner layer or multiple layers of a cationic polyelectrolyte carrier.

17. The method of claim 16, wherein the outermost layer of a cationic polyelectrolyte carrier is more hydrophobic and/or more cationic than the inner layer or multiple layers of a cationic polyelectrolyte carrier.

18. The medical device of claim 15, wherein the inner layer or multiple layers of a cationic polyelectrolyte carrier comprises human serum albumin, gelatin, chitosan, or a combination thereof.

19. The medical device of claim 15, wherein the medical device comprises a stent, a catheter, a balloon catheter, or a combination thereof.

20. The medical device of claim 15, wherein the at least one negatively charged therapeutic agent comprises rapamycin.

21. The medical device of claim 15, wherein the at least one negatively charged therapeutic agent comprises paclitaxel.

22. A method of delivering a therapeutic agent to a target location by implanting in the target location a medical device comprising at least one negatively charged therapeutic agent adsorbed on at least a portion thereof; wherein the medical device is produced by a process comprising:

(a) coating at least a portion of a medical device with a cationic polyelectrolyte carrier to form a layer of a cationic polyelectrolyte carrier;

(b) washing the layer of a cationic polyelectrolyte carrier with a washing solution;

(c) adsorbing at least one negatively charged therapeutic agent onto the layer of a cationic polyelectrolyte carrier to form a layer of at least one negatively charged therapeutic agent; and (d) washing the layer of at least one negatively charged therapeutic agent with a washing solution and repeating steps (a) through (c) one or more times to form multiple layers of a cationic polyelectrolyte carrier and therapeutic agent until a desired amount of at least one negatively charged therapeutic agent has been adsorbed onto the medical device.

23. The method of claim 22, further comprising the step of coating the outermost layer of the at least one negatively charged therapeutic agent with an outermost layer of a catiomc polyelectrolyte carrier which is the same or different from the inner layer or multiple layers of a cationic polyelectrolyte carrier.

24. The method of claim 23, wherein the outermost layer of a cationic polyelectrolyte carrier is more hydrophobic and/or more cationic than the inner layer or multiple layers of a cationic polyelectrolyte carrier.

25. The method of claim 22, wherein the inner layer or multiple layers of a cationic polyelectrolyte carrier comprises human serum albumin, gelatin, chitosan, or a combination thereof.

26. The method of claim 22, wherein the medical device comprises a stent, a catheter, a balloon catheter, or a combination thereof.

27. The method of claim 22, wherein the at least one negatively charged therapeutic agent comprises rapamycin.

28. The method of claim 22, wherein the at least one negatively charged therapeutic agent comprises paclitaxel.

29. The method of claim 22, wherein the target location comprises at least one location selected from the group consisting of brain, heart, liver, skeletal muscle, smooth muscle, kidney, bladder, intestines, stomach, pancreas, ovary, prostate, cartilage, bone, lung, blood vessel, ureter, urethra, and testes.

30. A method for treating the occurrence or severity of a clinical disease or condition, comprising:

(a) preparing a medical device by:

(i) coating at least one a portion of a medical device with a cationic polyelectrolyte carrier to form a layer of a cationic polyelectrolyte carrier;

(ii) washing the layer of a cationic polyelectrolyte carrier with a washing solution;

(iii) adsorbing at least one negatively charged therapeutic agent effective to treat or reduce the occurrence of the clinical disease or condition onto the layer of a cationic polyelectrolyte carrier to form a layer of at least one negatively charged therapeutic agent; and (iv) washing the layer of at least one negatively charged therapeutic agent with a washing solution and repeating steps (i) through (iii) one or more times to form multiple layers of a cationic polyelectrolyte carrier and at least one negatively charged therapeutic agent until a desired amount of at least one negatively charged therapeutic agent has been adsorbed onto the medical device; and (b) implanting the medical device into a target location in a mammal from which the at least one negatively charged therapeutic agent can treat or reduce the occurrence or severity of the clinical disease or condition.

31. The method of claim 30, comprising the step of coating the outermost layer of at least one negatively charged therapeutic agent with an outermost layer of a cationic polyelectrolyte carrier which is the same or different from the inner layer or multiple layers of a cationic polyelectrolyte carrier.

32. The method of claim 31, wherein the outermost layer of a cationic polyelectrolyte carrier is more hydrophobic and/or more cationic than the inner layer or multiple layers of a cationic polyelectrolyte carrier.

33. The method of claim 30, wherein the inner layer or multiple layers of a cationic polyelectrolyte carrier comprises human serum albumin, gelatin, chitosan, or a combination thereof.

34. The method of claim 30, wherein the medical device comprises a stent, a catheter, a balloon catheter, or a combination thereof.

35. The method of claim 30, wherein the clinical disease or condition comprises restenosis or angiogenesis and the at least one negatively charged therapeutic agent comprises rapamycin.

36. The method of claim 30, wherein the clinical disease or condition comprises a malignancy or malignant cell growth and the at least one negatively charged therapeutic agent comprises paclitaxel.

37. The method of claim 30, wherein the target location comprises at least one location selected from the group consisting of brain, heart, liver, skeletal muscle, smooth muscle, kidney, bladder, intestines, stomach, pancreas, ovary, prostate, cartilage, bone, lung, blood vessel, ureter, urethra, and testes.

38. The medical device of claim 1 wherein the at least one negatively charged therapeutic agent is selected from the group consisting of a: anti-thrombogenic protein, antioxidant compound, angiogenic protein, agent which blocks smooth muscle cell proliferation, anti-inflammatory agent, calcium entry blocker, antineoplastic/antiproliferative/antimitotic compound, anti-microbial compound, anesthetic agent, nitric oxide donor, anti-coagulant, vascular cell growth promoting protein, vascular cell growth protein inhibitor, vascular cell growth antibody inhibitor, cholesterol lowering drug, vasodilating drug, protein that protects against cell death, cell cycle CDK protein inhibitor, anti-restenosis protein, agent for treating malignancies, bone morphogenic protein, a polynucleotide encoding any of the above named proteins or protein inhibitors, and an adenovirus vector comprising a polynucleotide encoding any of the above named proteins or protein inhibitors.

39. The medical device of claim 38 wherein the anti-thrombogenic protein is heparin, heparin derivatives, urokinase, or PPACK.

40. The medical device of claim 38 wherein the antioxidant compound is probucol or retinoic acid.

41. The method of claim 8 wherein the at least one negatively charged therapeutic agent is selected from the group consisting of a: anti-thrombogenic protein, antioxidant compound, angiogenic protein, agent which blocks smooth muscle cell proliferation, anti-inflammatory agent, calcium entry blocker, antineoplastic/antiproliferative/antimitotic compound, anti-microbial compound, anesthetic agent, nitric oxide donor, anti-coagulant, vascular cell growth promoting protein, vascular cell growth protein inhibitor, vascular cell growth antibody inhibitor, cholesterol lowering drug, vasodilating drug, protein that protects against cell death, cell cycle CDK protein inhibitor, anti-restenosis protein, agent for treating malignancies, bone morphogenic protein, a polynucleotide encoding any of the above named proteins or protein inhibitors, and an adenovirus vector comprising a polynucleotide encoding any of the above named proteins or protein inhibitors.

42. The method of claim 41 wherein the anti-thrombogenic protein is heparin, heparin derivatives, urokinase, or PPACK.

43. The method of claim 41 wherein the antioxidant compound is probucol or retinoic acid.

44. The medical device of claim 15 wherein the at least one negatively charged therapeutic agent is selected from the group consisting of a: anti-thrombogenic protein, antioxidant compound, angiogenic protein, agent which blocks smooth muscle cell proliferation, anti-inflammatory agent, calcium entry blocker, antineoplastic/antiproliferative/antimitotic compound, anti-microbial compound, anesthetic agent, nitric oxide donor, anti-coagulant, vascular cell growth promoting protein, vascular cell growth protein inhibitor, vascular cell growth antibody inhibitor, cholesterol lowering drug, vasodilating drug, protein that protects against cell death, cell cycle CDK protein inhibitor, anti-restenosis protein, agents for treating malignancies, bone morphogenic protein, a polynucleotide encoding any of the above named proteins or protein inhibitors, and an adenovirus vector comorisina a polynucleotide encoding any of the above named proteins or protein inhibitors.

45. The medical device of claim 44 wherein the anti-thrombogenic protein is heparin, heparin derivatives, urokinase, or PPACK.

46. The medical device of claim 44 wherein the antioxidant compound is probucol or retinoic acid.

47. The method of claim 22 wherein the at least one negatively charged therapeutic agent is selected from the group consisting of a: anti-thrombogenic protein, antioxidant compound, angiogenic protein, agent which blocks smooth muscle cell proliferation, anti-inflammatory agent, calcium entry blocker, antineoplastic/antiproliferative/antimitotic compound, anti-microbial compound, anesthetic agent, nitric oxide donor, anti-coagulant, vascular cell growth promoting protein, vascular cell growth protein inhibitor, vascular cell growth antibody inhibitor, cholesterol lowering drug, vasodilating drug, protein that protects against cell death, cell cycle CDK protein inhibitor, anti-restenosis protein, agent for treating malignancies, bone morphogenic protein, a polynucleotide encoding any of the above named proteins or protein inhibitors, and an adenovirus vector comprising a polynucleotide encoding any of the above named proteins or protein inhibitors.

48. The method of claim 47 wherein the anti-thrombogenic protein is heparin, heparin derivatives, urokinase, or PPACK.

49. The method of claim 47 wherein the antioxidant compound is probucol or retinoic acid.

50. The method of claim 30 wherein the at least one negatively charged therapeutic agent is selected from the group consisting of a: anti-thrombogenic protein, antioxidant compound, angiogenic protein, agent which blocks smooth muscle cell proliferation, anti-inflammatory agent, calcium entry blocker, antineoplastic/antiproliferative/antimitotic compound, anti-microbial compound, anesthetic agent, nitric oxide donor, anti-coagulant, vascular cell growth promoting protein, vascular cell growth protein inhibitor, vascular cell growth antibody inhibitor, cholesterol lowering drug, vasodilating drug, protein that protects against cell death, cell cycle CDK protein inhibitor, anti-restenosis protein, agentfor treating malignancies, bone morphogenic protein, a polynucleotide encoding any of the above named proteins or protein inhibitors, and an adenovirus vector comprising a polynucleotide encoding any of the above named proteins or protein inhibitors.

51. The method of claim 50 wherein the anti-thrombogenic protein is heparin, heparin derivatives, urokinase, or PPACK.

52. The method of claim 50 wherein the antioxidant compound is probucol or retinoic acid.

53. A method of delivering a therapeutic agent to a mammal, the method comprising implanting a medical device at a desired location or tissue in a mammal, wherein the medical device is produced by a process comprising:
   (a) coating at least a portion of the medical device with a cationic polyelectrolyte carrier to form a layer of a cationic polyelectrolyte carrier;
   (b) washing the layer of a cationic polyelectrolyte carrier with a washing solution;
   (c) adsorbing at least one negatively charged therapeutic agent onto the layer of a cationic polyelectrolyte carrier to form a layer of at least one negatively charged therapeutic agent; and
   (d) washing the layer of at least one negatively charged therapeutic agent with a washing solution and repeating steps (a) through (c) one or more times to form multiple layers of a cationic polyelectrolyte carrier and at least one negatively charged therapeutic agent until a desired amount of at least one negatively charged therapeutic agent has been adsorbed onto the medical device.

54. A method of delivering a polynucleotide encoding a protein to a mammal, the method comprising implanting a medical device at a desired location or tissue in a mammal, wherein the medical device is prepared by:
   (i) coating at least a portion of the medical device with a cationic polyelectrolyte carrier to form a layer of a cationic polyelectrolyte carrier;
   (ii) washing the layer of a cationic polyelectrolyte carrier with a washing solution;
   (iii) adsorbing at least one negatively charged therapeutic agent onto the layer of a cationic polyelectrolyte carrier to form a layer of at least one negatively charged therapeutic agent; and
   (iv) washing the layer of at least one negatively charged therapeutic agent with a washing solution and repeating steps (i) through (iii) one or more times to form multiple layers of a cationic polyelectrolyte carrier and at least one negatively charged therapeutic agent until a desired amount of the at least one negatively charged therapeutic agent has been adsorbed onto the medical device, wherein the at least one negatively charged therapeutic agent is a polynucleotide encoding a protein.

55. A method of delivering a DNA encoding a therapeutic protein to a mammal, the method comprising implanting a medical device at a desired location or tissue in a mammal, wherein the medical device is prepared by:
   (i) coating at least a portion of the medical device with a cationie polyelectrolyte carrier to form a layer of a cationic polyelectrolyte carrier;
   (ii) washing the layer of a cationic polyelectrolyte carrier with a washing solution;
   (iii) adsorbing at least one negatively charged therapeutic agent onto the layer of a cationic polyelectrolyte carrier to form a layer of at least one negatively charged therapeutic agent; and
   (iv) washing the layer of at least one negatively charged therapeutic agent with a washing solution and repeating steps (i) through (iii) one or more times to form multiple layers of cationic polyelectrolyte carrier and at least one negatively charged therapeutic agent until a desired amount of at least one negatively charged therapeutic agent has been adsorbed onto the medical device, wherein the at least one negatively charged therapeutic agents is a DNA encoding a therapeutic protein, wherein the therapeutic protein is selected from the group consisting of a anti-thrombogenic protein, angiogenic protein, vascular cell growth promoting protein, vascular cell growth protein inhibitor, protein that protectsagainst cell death, cell cycle CDK protein inhibitor, anti-restenosis protein and a bone morphogenic protein.

56. A method for inhibiting restenosis or the growth of tumor cells in a mammal, comprising:
   (a) preparing a medical device by:
      (i) coating at least a portion of the medical device with a cationic polyelectrolyte carrier to form a layer of a cationic polyelectrolyte carrier;
      (ii) washing the layer of a cationic polyelectrolyte carrier with a washing solution;
      (iii) adsorbing at least one negatively charged therapeutic agent effective to inhibit restenosis or the growth of tumor cells onto the layer of a cationic polyelectrolyte carrier to form a layer of at least one negatively charged therapeutic agent; and
      (iv) washing the layer of negatively charged therapeutic agent with a washing solution and repeating steps (i) through (iii) one or more times to form multiple layers of a cationic polyelectrolyte carrier and at least one negatively charged therapeutic agent until a desired amount of at least one negatively charged therapeutic agent has been adsorbed onto the medical device; and
   (b) implanting the medical device into a target location in a mammal, wherein the at least one negatively charged therapeutic agent is a DNA coding for an anti-proliferative protein.

57. A method for inducing the growth of blood vessels at a target location in a mammal, comprising:
   (a) preparing a medical device by:
      (i) coating at least a portion of the medical device with a cationic polyelectrolyte carrier to form a layer of a cationic polyelectrolyte carrier;
      (ii) washing the layer of a cationic polyelectrolyte carrier with a washing solution;

(iii) adsorbing at least one negatively charged therapeutic agent effective to induce the growth of blood vessels onto the layer of a cationic polyelectrolyte carrier to form a layer of at least one negatively charged therapeutic agent; and
(iv) washing the layer of at least one negatively charged therapeutic agent with a washing solution and repeating steps (i) through (iii) one or more times to form multiple layers of a cationic polyelectrolyte carrier and at least one negatively charged therapeutic agent until a desired amount of the least one negatively charged therapeutic agent has been adsorbed onto the medical device; and (b) implanting the medical device into the target location in a mammal, wherein the at least one negatively charged therapeutic agent is a DNA coding for an angiogenic protein.

* * * * *

UNITED STATES PATENT AND TRADEMARK OFFICE
CERTIFICATE OF CORRECTION

PATENT NO. : 6,899,731 B2
DATED : May 31, 2005
INVENTOR(S) : Li et al.

It is certified that error appears in the above-identified patent and that said Letters Patent is hereby corrected as shown below:

Column 5,
Line 22, change "andnitorfurantoin" to -- and nitrofurantoin --;
Line 25, change "lisidomine" to -- linsidomine --;
Line 31, change "Warafin" to -- Warfarin --;
Lines 33 and 35, change "promotors" to -- promoters --;
Line 43, delete blank line/close up;
Line 44, change "endogeneus" to -- endogenous --;

Column 6,
Line 45, change "deliyery" to -- delivery --;

Column 7,
Line 13, change "HAS" to -- HSA --;
Line 25, change "coaating" to -- coating --;

Column 14,
Line 38, change "catiomc" to -- cationic --;

Column 16,
Line 41, change "comorisina" to -- comprising --;

Column 17,
Line 5, change "agentfor" to -- agent for --;

UNITED STATES PATENT AND TRADEMARK OFFICE
CERTIFICATE OF CORRECTION

PATENT NO. : 6,899,731 B2
DATED : May 31, 2005
INVENTOR(S) : Li et al.

It is certified that error appears in the above-identified patent and that said Letters Patent is hereby corrected as shown below:

Column 18,
Line 7, change "cationie" to -- cationic --;
Line 30, change "protectsagainst" to -- protect against --.

Signed and Sealed this

Twenty-fourth Day of January, 2006

JON W. DUDAS
*Director of the United States Patent and Trademark Office*